(12) United States Patent
Kelly

(10) Patent No.: US 6,702,735 B2
(45) Date of Patent: Mar. 9, 2004

(54) DEVICE FOR MOVEMENT ALONG A PASSAGE

(75) Inventor: Leonard Kelly, Peterborough (CA)

(73) Assignee: Charlotte Margaret Kelly, Peterborough (CA)

(*) Notice: Subject to any disclaimer, the term of this patent is extended or adjusted under 35 U.S.C. 154(b) by 214 days.

(21) Appl. No.: 09/975,941

(22) Filed: Oct. 15, 2001

(65) Prior Publication Data

US 2002/0045906 A1 Apr. 18, 2002

Related U.S. Application Data

(60) Provisional application No. 60/240,846, filed on Oct. 17, 2002.

(51) Int. Cl.$^7$ ................................................. A61B 1/04
(52) U.S. Cl. ....................................... 600/115; 606/108
(58) Field of Search ..................... 606/108; 600/116, 600/106, 114, 115; 604/271

(56) References Cited

U.S. PATENT DOCUMENTS

| | | |
|---|---|---|
| 3,911,927 A | 10/1975 | Rich et al. |
| 4,148,307 A | 4/1979 | Utsugi |
| 4,207,872 A | 6/1980 | Meiri et al. |
| 4,243,033 A | 1/1981 | DeCaprio et al. |
| 4,321,915 A | 3/1982 | Leighton et al. |
| 4,615,331 A | 10/1986 | Kramann |
| 4,676,228 A * | 6/1987 | Krasner et al. ............. 600/116 |
| 4,685,473 A | 8/1987 | Karcher et al. |
| 4,690,131 A | 9/1987 | Lyddy, Jr. et al. |
| 4,871,358 A | 10/1989 | Gold |
| 4,934,786 A | 6/1990 | Krauter |
| 5,144,848 A | 9/1992 | Uenishi et al. |
| 5,176,636 A | 1/1993 | Wild |
| 5,236,423 A | 8/1993 | Mix et al. |
| 5,259,364 A * | 11/1993 | Bob et al. .................... 600/115 |
| 5,259,368 A | 11/1993 | Wiksell |
| 5,353,783 A | 10/1994 | Nakao et al. |
| 5,364,353 A | 11/1994 | Corfitsen et al. |
| 5,454,364 A | 10/1995 | Krüger |
| 5,496,259 A | 3/1996 | Perkins |
| 5,569,183 A | 10/1996 | Kieturakis |
| 5,586,968 A | 12/1996 | Gründl et al. |
| 5,601,589 A | 2/1997 | Fogarty et al. |
| 5,762,604 A | 6/1998 | Kieturakis |
| 6,004,328 A * | 12/1999 | Solar .......................... 623/1.11 |
| 6,007,483 A | 12/1999 | Kieturakis |
| 6,039,721 A * | 3/2000 | Johnson et al. ............. 604/508 |
| 6,293,907 B1 * | 9/2001 | Axon et al. ................. 600/114 |
| 6,478,807 B1 * | 11/2002 | Foreman et al. ........... 606/194 |
| 2001/0016753 A1 * | 8/2001 | Caprio et al. ............... 606/192 |

FOREIGN PATENT DOCUMENTS

| | | |
|---|---|---|
| CA | 2170729 | 3/1995 |
| EP | 0 873 761 A1 | 10/1998 |
| WO | WO 94/24934 | 11/1994 |
| WO | WO 99/17828 | 4/1999 |
| WO | WO 00/29057 | 5/2000 |

* cited by examiner

Primary Examiner—Eduardo C. Robert
(74) Attorney, Agent, or Firm—Thomas Adams

(57) ABSTRACT

A device for moving a tool along a passage, particularly for use in medical procedures, has two different aspects. In one aspect, a tool, e.g. a colonoscope, is surrounded by a sheath. The sheath has an inflatable region for engaging the passage wall, e.g. a colon. An annular extension region of the sheath is provided which becomes part of the inflated inflatable region thereby increasing its length as the fluid pressure acts against a head of a tool to draw the tool along the passage. The annular extension region has sheath parts which face one another by their relative orientation caused by crumpling of the extension region, or the sheath parts are provided by folded portions. The extension region moves together with the tool as the sheath parts sequentially move into the inflated inflatable region. In the other aspect, after inflation of the inflatable region of the sheath, inflation pressure acts against an inflatable head carried at the distal end region of the tool to draw the tool along the passage.

20 Claims, 3 Drawing Sheets

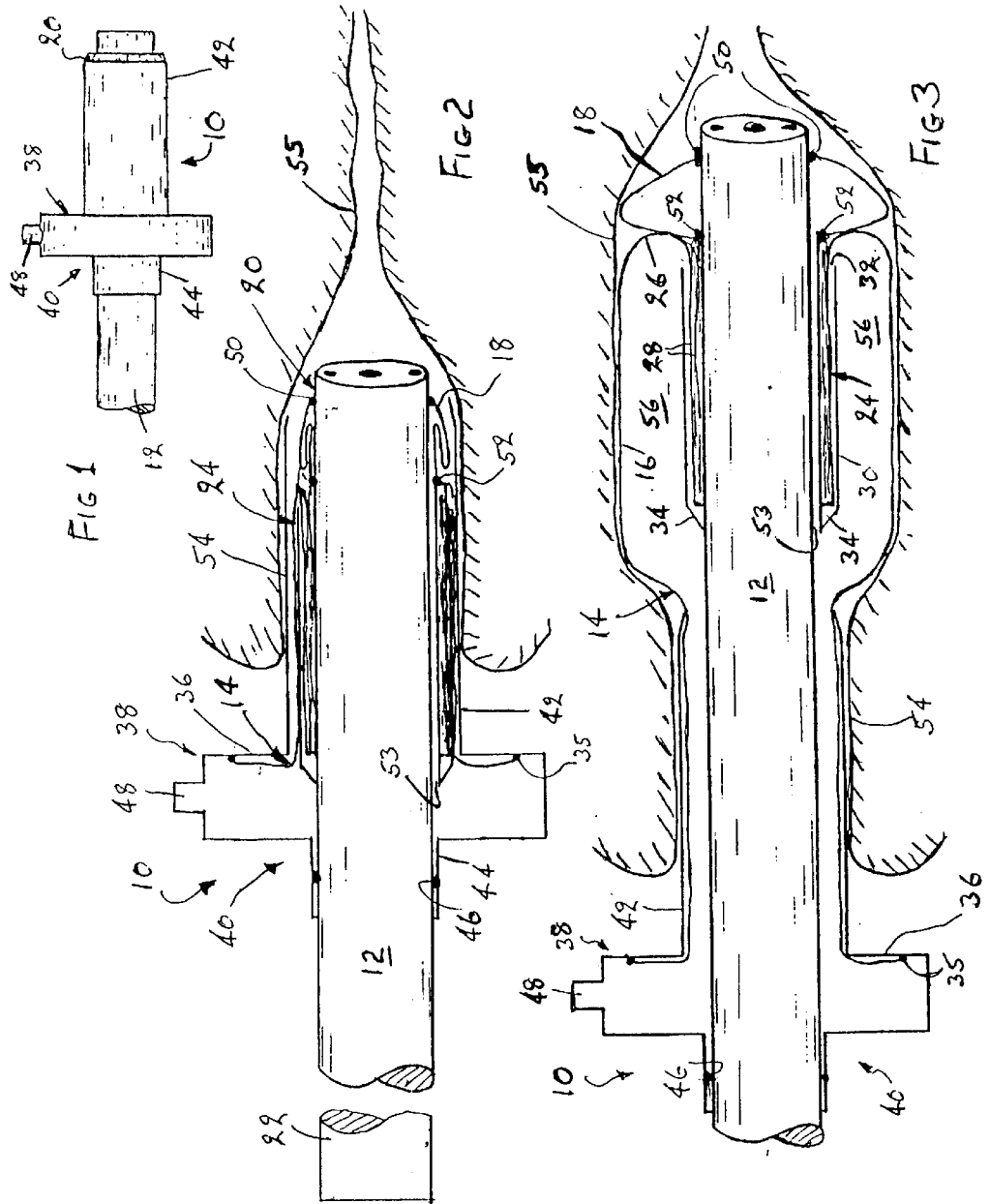

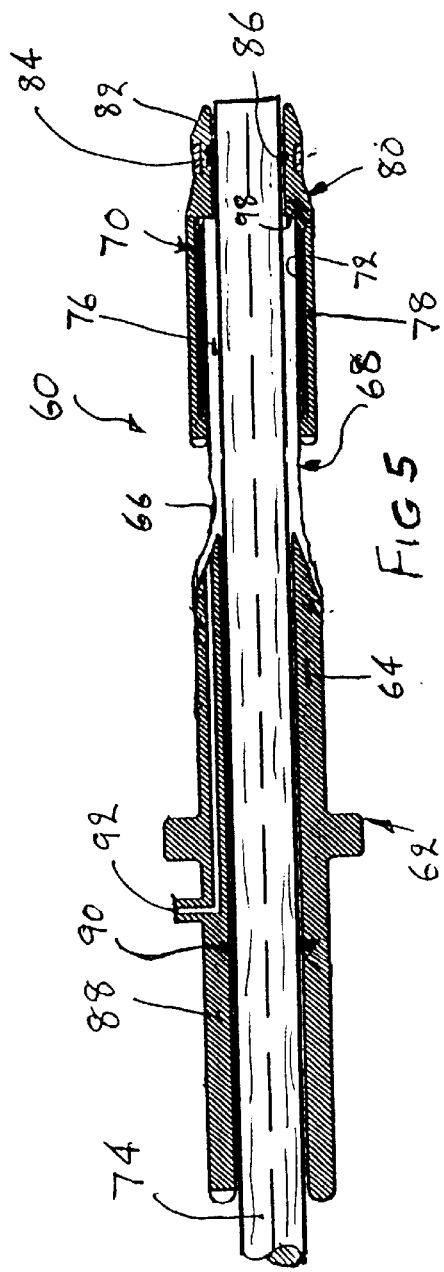
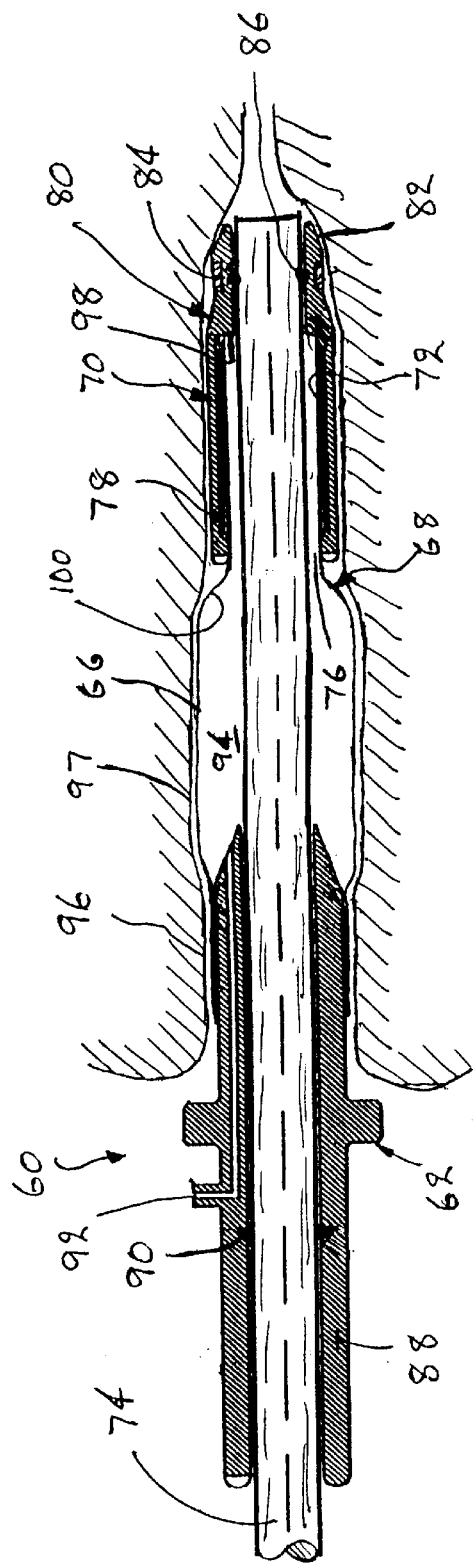

DEVICE FOR MOVEMENT ALONG A PASSAGE

This application claims the benefit of U.S. Provisional Application No. 60/240,846, filed Oct. 17, 2000.

FIELD OF THE INVENTION

This invention relates to devices for movement along passages.

BACKGROUND ART

Devices are generally known applicable in use for movement along passages, e.g. passages which require examination or certain treatments. In particular, devices are made which are intended for use in medical procedures, i.e., when the devices are for movement along passages of humans and animals. In this latter regard, such devices may include, for instance, a sound, a colonoscope, catheter or endoscope.

It is generally accepted that the use of any device of the above or similar medical type upon their persons, is not welcomed by patients who, while accepting that the use of such devices is necessary, face their usage with physical and emotional repulsion. Feelings of humiliation and personal degradation may also occur, particularly during the use of a colonoscope. These feelings and fears, together with the fear of diagnosis, can cause great tension and resulting spasm, which could contribute to problems during the procedure, and possibly cause pain.

However, of primary importance during the use of a colonoscope is the avoidance of injury to the patient and the completion of procedures in a safe and speedy manner, and in a predictable time. With this in mind, and in order to alleviate the above problems, many colonoscope procedures are performed under a light anaesthetic which includes an amnesiac component. This results firstly in the patient being able to report pain during the procedure, when he feels it, while ideally not feeling the pain sensations afterwards. Secondly, it warns medical staff of impending difficulties.

Many colonoscopic procedures are routinely performed without undue difficulty at present, but a certain percentage are complicated and cannot be completed with known devices. In addition, known devices may present problems in successfully negotiating twists and turns in a colon. This adds to an inordinately lengthy average procedure time, which adds to the stress of both the patient and the attendant medical staff. The lengthy procedure time results, on average, in colonoscope procedures being undesirably expensive, whether or not they are successfully completed.

In attempts to mitigate all of the above fears, various types of constructions of device have been used and suggested. In one basic type of construction of device, a flexible sheath for covering an elongate diagnostic or surgical tool is provided on its outer surface with inflatable devices sequentially positioned along the sheath. These inflatable devices, sometimes with elastic means extending between them, are inflated and deflated in predetermined order to effect movement of the sheath along the passage. Such movement is slow and intermittent and, it is believed, the continual inflation and deflation of the inflatable devices into and out of contact with the colon wall, must add to patient discomfort. Examples of this type of device are described in U.S. Pat. Nos. 4,148,307 and 4,676,228. In another basic type of construction, an elongate sheath is everted during inflation to urge a tool contained within the sheath along the passage. With this type of construction, in order to evert the sheath, the sheath must have a radially outer region inflated into contact with the passage wall, and a radially inner region which contacts the surface of the tool. However, a problem which is inherent in use of this construction is that the radially inner region of the sheath must move relative to, and upon, the surface of the tool during the eversion procedure in feeding the tool along the passage. This relative movement produces frictional resistance to movement of the device along a passage, e.g. a colon, which adds difficulty to exploratory or surgical procedures. Frictional resistance is exacerbated by inflation pressure forcing the radially inner region against the tool surface. This produces severe problems concerning freedom of movement of the device, particularly around turns and restrictions of the colon. Prior U.S. Pat. No. 5,259,364 acknowledges that the radially inner region of an eversible tube travels at twice the speed of an endoscope to move the endoscope along a colon passage. In the disclosure, it is stated that to obtain substantially no frictional forces between the tube and endoscope, fluid under pressure is directed between the radially inner region of the tube and the endoscope to space them apart.

SUMMARY OF THE INVENTION

The present invention seeks to provide a device for movement along a passage which lessens the above problems in use. When used for medical purposes, the device of the invention seeks to avoid injury to the patient while enabling completion of procedures in a safe and speedy manner and in a predictable time.

According to one aspect of the invention, there is provided a device for movement along a passage comprising:

elongate tool having a major axis, distal and proximal end regions, and a sheath abutment element at the distal end region of the tool;

an elongate inflatable sheath surrounding the tool, the sheath having an annular inflatable region disposed between the abutment element and the proximal end region of the tool, and an annular extension region for the annular inflatable region, the annular extension region having a plurality of sequentially interconnected sheath parts extending from the inflatable region, the sheath parts being relatively oriented to face each other to locate the annular extension region around the distal end region of the tool with the annular extension region movable forwardly together with the distal end region of the tool;

an annular inflation chamber defined between the inflatable region and the outer surface of the tool; and means for introducing pressurized fluid into the chamber to inflate the inflatable region of the sheath, when inside the passage, and to cause inflationary pressure then to act against the sheath abutment element to move the tool forwardly along the passage accompanied by sequential reorientation of the sheath parts and their sequential movement into, and lengthen, the inflatable region.

When the device of the invention defined above is to be used within passages provided by inanimate matter, these passages would normally be expected to be provided with a rigid wall, e.g. in the case of metal or plastic pipes. In such a case, the radially outwards expansion of the inflatable region of the sheath would be constrained by the rigid wall and the sheath would have to expand axially, upon continued introduction of the pressurized fluid, so that the tool was moved along the passage. Where, however, the device is to be used upon living beings, particularly humans, then the sheath should have limited radial expansion, i.e., to a desired maximum. The sheath may be formed from an inelastic material, such as an inelastic polymer, e.g. polyurethane film. Alternatively, the sheath may include a plurality of longitudinally inextensible fibers which are oriented in at least one particular direction for the purpose of limiting radial expansion. Hence, the sheath should be designed so as not to apply undue pressure to the wall of the passage, e.g. a colon, but may apply sufficient pressure either merely to engage the passage wall or with a small acceptable radial enlargement of the passage. Thus the sheath will grip the passage wall and then expand progressively along its length while, simultaneously, the tool, e.g. a colonoscope, is moved forwardly by the inflationary pressure. When the device is used for medical purposes, the limit to radial expansion of the sheath thus may help to lessen any discomfort and anxiety of a patient. Sudden increases and decreases of inflationary pressure at localized regions of the passage are avoided, such as must be provided by devices having inflatable bags inflated and deflated in specified order to move a tool incrementally along the passage.

In addition to the above, and to render the device of the invention more easily useable in medical situations, and therefore to make use of the device more acceptable to a patient, ease of movement of the tool along the passage is maximized. This is because frictional resistance to movement between relatively moveable parts of the device is minimized. Hence, when required, such as for colonoscope use, movement along curved tortuous regions of the colon is made easier, thereby increasing chances of full traverse to the caecum. Minimization of the frictional resistance is effected by having the inflation chamber defined partly by the tool outer surface so that the sheath does not have a radially inner portion which must slide upon the tool surface and which would create frictional resistance.

In contrast to having a radially inner portion of sheath sliding upon the tool surface, a structure of the above invention has, instead, the annular extension region which moves forwardly along the passage together with and at the same rate as the tool. The sheath parts of the extension region are deployed from the distal end of the tool.

In one arrangement, the annular extension region is connected to the inflatable region by a distal end fold of the sheath. The distal end fold preferably engages the sheath abutment element and under inflation pressure, the sheath everses by the distal end fold rolling forwardly under inflation forces acting against the abutment element thereby urging the tool forwardly. The annular extension region progressively moves through the distal end fold, as it rolls forwardly, to progressively become part of the axially lengthening inflatable region of the sheath. The annular extension region in this arrangement, may be supported radially inwards upon the tool, and may be contained within a cylindrical housing secured around the tool.

In another arrangement, the sheath has a minimum radius of collapse whereby the annular extension region is disposed at a larger diameter than a region of the tool which is located radially within the extension region. In this case, means is required to maintain the extension region spaced by an annular gap from that region of the tool. It is convenient if this spacing-maintaining means comprises an axially extending part of the abutment element and which is itself spaced from the above region of the tool. In a practical structure, this part of the abutment element contains and supports the extension region to restrain it from radial outward expansion under inflation pressure, and until each sheath part of the extension region moves into and becomes part of the inflatable region of the sheath as forward movement proceeds. In this practical structure, the extension region is thus located forwardly of the inflatable region of the sheath with a radially extending interconnecting sheath portion located intermediate the inflatable region and the extension region. During inflation, the sheath parts move sequentially radially outwardly into the inflatable region. With this structure, inflation pressure acts, not only to inflate the inflatable region, but also directly through an annular gap between the extension region of the sheath and the tool to be applied directly against the abutment element to move the tool forwardly. Thus, inflation forces do not act against the abutment element through the intermediary of a distal end fold as in the arrangement of the invention previously discussed. Hence, creation of any friction forces which may be caused by sliding of such a fold against the abutment element during sheath eversion is avoided.

The annular extension region may have its sheath parts provided by a plurality of sequentially interconnected annular folded portions positioned around the distal end region of the tool. The folded portions are caused to sequentially unfold as inflationary pressure acts against the sheath abutment element so as to move the folded portions into and progressively lengthen the inflated inflatable region. Alternatively, the annular extension region is crumpled to form the sheath parts. Crumpling is progressively removed as inflationary pressure acts against the sheath abutment element to move the sheath parts into the inflated inflatable region. In a case where the extension region is provided by annular folded portions, these are preferably positioned radially outside of, and are superimposed upon, one another. In the above arrangement employing a distal end fold and where the extension region has annular folded portions superposed upon one another, it is preferable for the folded portions to unfold sequentially, during eversion, radially inwardly from the radially outermost folded region. Hence, no slippage of the sheath upon the tool occurs during unfolding and unnecessary frictional resistance to movement of the tool is avoided.

According to a further aspect of the invention, there is provided a device for movement along a passage comprising:

an elongate tool having a major axis, distal and proximal end regions, and an inflatable sheath abutment element at the distal end region of the tool;

an elongate inflatable sheath surrounding the tool, the sheath having an annular inflatable region disposed between the abutment element and the proximal end region of the tool and an annular extension region interconnected with the annular inflatable region;

an annular inflation chamber defined within the annular inflatable region of the sheath; and means for introducing pressurized fluid both into the chamber to inflate the inflatable region of the sheath and the sheath abutment element, when inside the passage, and, with the abutment element inflated, to cause inflationary pressure to act against the sheath abutment element to draw the tool forwardly along the passage accompanied by progressive movement of the annular extension region of the sheath into the inflated region so as to increase the length of the inflated inflatable region.

The sheath and the abutment element are preferably both inflatable by limited amounts, which conveniently are to approximately equal outside diameters. Advantageously, after complete insertion of the device into the passage for whatever purpose, both the sheath and the abutment element may be deflated for easy removal. When the device is used in medical exploration and/or surgery, the ease of insertion and removal minimizes injury to the patient while adding to patient comfort and reduces possibility of pain and injury. In addition, the inflatable sheath abutment element is of a flexible nature and may deform somewhat according to change in shape of the passage. This provides a cushioning effect when contacting the wall of the passage, e.g. colon, so as to comply, at least to a degree, to the shape of the wall, thereby reducing resistance to forward movement along the passage while minimizing pain such as may be caused by colon distortion.

BRIEF DESCRIPTION OF THE DRAWINGS

Embodiments of the invention will now be described, by way of example, with reference to the accompanying drawings, in which:

FIG. 1 is a side elevational view of a device for medical use, and according to a first embodiment;

FIGS. 2 and 3 are cross-sectional views in side elevation, to a larger scale than FIG. 1, and showing two stages in operation of the device of the first embodiment;

FIG. 5 is a cross-sectional view in side elevation of a device for medical use according to a third embodiment; and FIG. 6 is a view similar to FIG. 3 showing one stage in use of the device of the third embodiment.

DESCRIPTION OF PREFERRED EMBODIMENTS

Figure 4:
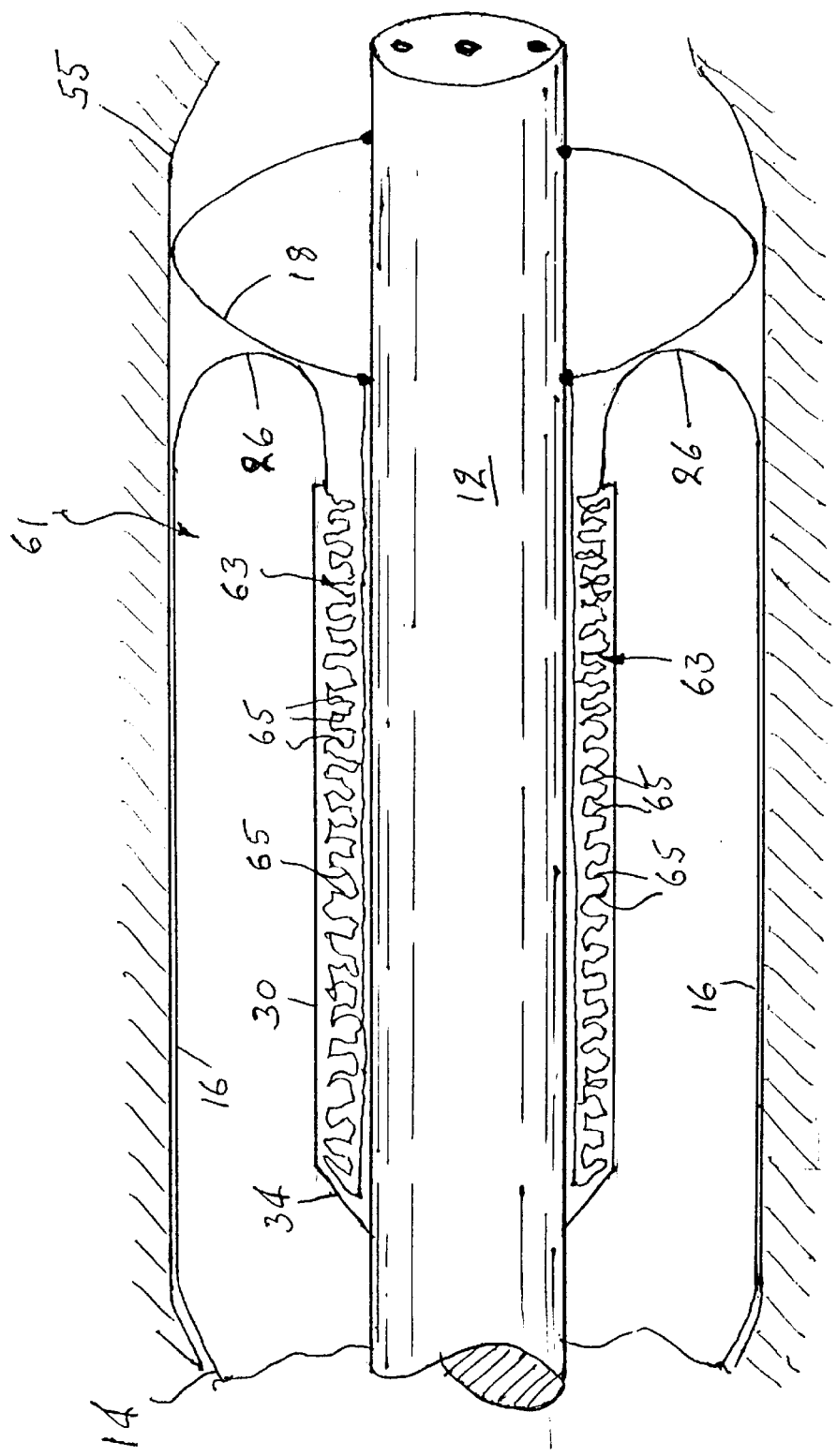
FIG. 4 is a cross-sectional view, in side elevation, and to a much larger scale, of part of a device according to a second embodiment.

In a first embodiment, as shown in FIGS. 1, 2 and 3, a device for movement along a passage comprises a colonoscopy device 10. This device has a flexible elongate tool in the form of a colonoscope 12 and an elongate inflatable sheath 14. As shown particularly in FIG. 3 for clarity, the sheath 14 has an annular inflatable region 16 surrounding the colonoscope 12. The annular inflatable region is disposed axially between a proximal end region 22 (FIG. 2) of the device and a sheath abutment element 18 disposed at a distal end region 20 of the device. The inflatable region 16 is connected to an annular extension region 24 by a distal end fold 26 of the sheath so as to render the sheath eversible. The extension region 24 comprises a plurality of sequentially interconnected sheath parts extending from the inflatable region 16. These sheath parts are in the form of axially extending folded portions 28 positioned radially outside of, and superposed upon, one another. The folded portions 28 are carried upon the surface of the colonoscope 12.

The sheath is necessarily of a material which is compatible with the wellbeing of a patient, e.g. a polymeric material, such as polyurethane film of suitable thickness for its purposes. This material is inelastic and is transparent. The sheath may have a thickness of 5 mil or less (e.g. down to 1 mil) is envisaged. The non-inflated sheath occupies a very small space (FIGS. 1 and 2). For example, the material of the sheath of 2 mil thickness having a 1 inch maximum inflatable diameter and 36 inches long would occupy approximately 0.216 cubic inches.

The extension region 24 is contained within a cylindrical housing 30 surrounding the colonoscope 12 adjacent the abutment element 18. The housing 30 has an opening 32 at its distal end for release of the folded portions 28. The other end of the housing 30 is secured by an end wall 34 to the colonoscope 12. The housing is flexible and moveable in conjunction with the colonoscope. The inflatable region 16 of the sheath 14 is sealingly secured at its proximal end at a position 35 to a radially extending wall 36 of a large diameter housing 38 of a smooth surfaced and rigid structure 40. This structure also includes a smaller diameter rectal insert 42 of cylindrical shape which extends towards the distal end of, but is radially spaced from, the colonoscope 12. Extending in the opposite direction from the rectal insert 42 is short sleeve 44 of the structure 40. The sleeve has a pressure seal 46 sealingly engaging the colonoscope 12 while allowing for axial movement of the colonoscope. The housing 38 has an inlet 48 for pressurized fluid for inflating the sheath 14. The pressurized fluid may be any suitable for the particular purpose in use of the device, e.g. air, water or an oil which is harmless to the patient should a leakage occur.

The abutment element 18 is itself inflatable and is formed by a non-elastic transparent material wall which may also be polyurethane of minimal thickness. The abutment element 18 is sealingly attached to the outer wall of the colonoscope 12 at upstream and downstream positions 50 and 52. The radially innermost folded portion 28 of the sheath also is sealingly attached to the colonoscope at position 52. The abutment element 18 is inflatable simultaneously with the sheath 14 through a passage 53 defined between the cylindrical housing 30 and the colonoscope 12.

As shown in FIGS. 1 and 2, before use, the colonoscope 12 is in a withdrawn position with its distal end located substantially completely within the rectal insert 42 and with the sheath 14 and the abutment element 18 collapsed and also within the rectal insert.

At commencement of a medical examination of the colon 55, the rectal insert is inserted into the rectum 54 of a patient and expands the walls of the rectum, as shown in FIG. 2, to the diameter of the insert (approximately 1 inch). Pressurized fluid is then passed through the inlet 48. This fluid flows inside the annular inflatable region 16 of the sheath, i.e. into an inflation chamber 56 (FIG. 3) defined between the inflatable region 16 and the surface of the colonoscope 12. Pressurized fluid also flows along the passage 53 to inflate the abutment element 18.

As the pressurized fluid continues to flow into the chamber 56, the inflatable region 16 inflates closely into contact with the inner surface of the rectal insert 42. Afterwards, the distal end fold 26 is moved by the inflation pressure in the distal direction to contact the abutment element 18 which by now has been inflated into contact with the rectal insert 42. The distal end fold then forces the abutment element 18 into the colon 55 and away from the rectal insert 42, the abutment element 18 drawing the colonoscope 12 with it. The leading folded portion 28 of the inflating sheath then emerges from the housing 30, followed in turn by the other folded portions, and each inflates to its maximum diameter of approximately 1 inch to grip and slightly expand the colon wall, while avoiding undue stress to the patient (FIG. 3). After the sheath inflatable region 16 outside the insert 42 has reached maximum diameter, the distal end fold 26 then continues to move downstream under the inflation pressure so as to push the abutment element 18 progressively in front of it along the colon. The colonoscope is pulled along the colon by the abutment element. During the whole movement of the distal end fold 26 in this manner, the inflated inflatable region of the sheath 16 progressively increases in length along the colon as the folded portions 28 unfold sequentially, from the radially outermost folded portion. The material of the folded portions 28 passes through the distal end fold to become part of the inflated inflatable region 16. The distal end fold 26 thus slides upon the abutment element 18 as it moves it and the colon along the passage.

During this procedure, the distal end region 20 of the colonoscope is held away from the colon wall by the sheath 14 so that it cannot contact the colon wall to cause injury or discomfort to the patient. Also, as the inflatable region 16 is being progressively lengthened, it continuously increases its length of contact with the colon wall with a rolling action by sheath material passing through the distal end fold 26. Consequently, there is no sliding action upon the colon wall, the colon wall being progressively expanded slightly as sheath movement continues. Thus, sliding of the sheath along the colon wall, together with rubbing action, is avoided, thereby reducing pain and discomfort to the patient.

Of extreme importance in one aspect of the invention, and as is exemplified by this embodiment, are the results achieved with the inflation chamber being defined between the sheath 14 and the colonoscope surface. The sheath does not have an inner wall for providing material to lengthen the inflatable region of the sheath and which would frictionally slidably engage the colonoscope 12 as it causes it to move forwards at the same speed as that of the distal end fold 26. Such frictional engagement would render the movement of the device along the colon unduly difficult when it is realized that the frictional sliding engagement of any inner wall of the sheath upon the colonoscope would be increased by the inflation pressure upon the wall. In the case of this embodiment of the invention, such frictional resistance is avoided because the annular extension region 24 moves distally together with the colonoscope 12 as the folded portions are being unfolded. This allows the device to move along the colon with maximized ease and to successfully negotiate any turns and curved regions of the colon. The device 10 of this embodiment may be traversable to the caecum with minimal discomfort and pain to the patient.

The inflation medium may, for instance, be air or water or even an oil suitable for this particular purpose. Where oil is used, it would provide a welcome lubricant to facilitate movement of the colonoscope, the unfolding of the folded portions 28 of the sheath and the sliding of the distal end fold 26 upon the abutment 18.

The inflatable abutment element 18 has multiple functions including, in addition to the above, holding the sheath in position behind it during inflation, while preventing the sheath from expanding ahead of it. Also the element 18 increases ease and speed of operation while reducing resistance to forward movement along the passage while minimizing pain and discomfort. This element is inflatable to its maximum diameter approximately equal to that of the sheath 14. While the abutment element 18 assists in increasing the diameter of the colon as it moves along it, it has a flexibility which enables the element to be deformed to a certain degree by the surface shape of the colon wall. Thus, any changes to this shape as the abutment element moves along the colon, may be accommodated by some corresponding change in shape of the abutment element. Painful contact with certain regions of the colon is thus minimized. The flexibility of the abutment element also assists it in traversing corners or turns in the colon. Potentially maximizing speed of operation serves to minimize stress both to the patient and to the medical staff, while making it possible to reduce, perhaps significantly, the average cost of colonoscopy procedures and maximizing efficiency in use of medical staff.

Further, to assist in movement along the colon, the abutment element may be coated with a friction reducing material, e.g. it may be coated with polytetrafluoroethylene ("Teflon"). Such a low friction material will also reduce frictional resistance to the movement of the distal end fold 26 upon the abutment element 18.

It is estimated that a modest 6 pounds per square inch inflation pressure will create a forward thrust of 3 pounds force upon the abutment element which is sufficient to draw the colonoscope 12 through the colon.

After the medical procedure has been accomplished, the sheath 14 and abutment element 18 are both deflated down onto the surface of the colonoscope 12 to allow for ease of withdrawal of the device while further minimizing discomfort or damage to the patient.

As may be seen from the above description, normal colonoscopic operation, i.e. video and instrument operation, may be fully operational with the above device.

In a second embodiment, as shown by FIG. 4, a colonoscope device 61 is basically of the same construction as the device of the first embodiment and like reference numbers are used for similar parts. The structure differs from that of the first embodiment in that the sheath 14 has an annular extension region 63 which is scrunched up, i.e. crumpled, in the axial direction so as to axially shorten the sheath material in the extension region whereby it lies within the housing 30. The crumpling action forms sequentially interconnected sheath parts 65 which are relatively oriented to face each other within the housing 30. These sheath parts 65 are of random size, shape and direction such as is provided by a crumpling action. The crumpled structure is shown in FIG. 4, more open, for clarity, than would be expected in practice.

In use of the device of the second embodiment, during inflation of the sheath, fluid pressure acts against the distal end fold 26, as in the first embodiment, to cause the fold to roll upon the inflated abutment element 18 and urge the colonoscope 12 along colon 55. During this rolling action the sheath parts 65 are moved sequentially out of the housing to become relatively reoriented by uncrimpling of sheath material, the sheath parts then moving through the distal end field to become parts of the lengthening inflated inflatable region 16.

In a third embodiment, as shown in FIGS. 5 and 6, a colonoscopic device 60 comprises a rigid structure 62 comprising a rectal insert 64. The insert 64 has an outer cylindrical surface and is received within the proximal end section of an inflatable region 66 of a sheath 68. The sheath 68 is sealingly secured to the outer surface of the insert 64. The sheath has a annular extension region 70 comprising sequentially interconnected sheath parts in the form of a plurality of axially extending and overlying folded portions 72. The material of the sheath is similar to that of the sheath of the first embodiment and, while being inelastic, the folded portions 72 lie at a minimum diameter which is greater than the diameter of the colonoscope 74.

Means is provided for maintaining the folded portions 72 spaced by an annular gap 76 from the surface of the colonoscope. This space-maintaining means comprises an axially extending cylindrical part 78 of an abutment element 80 which holds the folded regions coaxially spaced around the colonoscope 74. The cylindrical part 78 extends rearwardly of a head 82 of the abutment element, the head extending radially inwardly to contact the surface of the colonoscope 74. The head is secured to the colonoscope by a locking collar 84 and a pressure seal 86 is disposed between the head and the colonoscope.

The abutment element 80 may be approximately 7 centimeters in length and is of a flexible and pliable plastic so as to be able to follow the turns and negotiate corners of a colon. The sheath may be coated with a low friction material, e.g. "Teflon".

The colonoscope 74 extends through a proximal end or handle 88 of the rigid structure 62 and is sealed therein by a pressure seal 90 which allows for axial movement of the colonoscope within the structure. An inlet 92 is provided in the rigid structure for supplying a pressurized fluid into an inflation chamber 94 between the inflatable region 66 of the sheath and the surface of the colonoscope 74.

In use, the device of the third embodiment has the advantages obtained in the first and second embodiments with regard to the inflation chamber being partly defined by the surface of the colonoscope. Thus, frictional resistance to movement of the colonoscope along a colon is minimized with the fluid directly contacting the colonoscope. Also, the inflatable region 66 of the sheath progressively increases in axial length along the colon while minimizing pain or discomfort to the patient. However, the sheath of the third embodiment operates differently from that of the first and second embodiments to increase the length of the inflatable region. Also, the method of applying inflation pressure to the abutment element is different. These differences will now be discussed.

In use of the device 60, and as shown by FIG. 6, after the rectal insert 64 has been inserted into the rectum 96 of a patient, pressurized fluid is introduced into the chamber 94 through the inlet 92. This fluid inflates the inflatable region 66 of the sheath to its maximum diameter so that it expands the colon 97 slightly. Continued inflation pressure then acts against a downstream end surface 98 of the head 82 of the abutment element to urge the abutment element along the colon. This pressure is applied through the gap 76 between the folded portions 72 and the colonoscope 74, the gap providing part of the chamber 94. Hence, the inflation pressure is applied directly against the abutment element 18 and not through the medium of the sheath itself. The structure therefore avoids the use of a distal end region of the sheath which moves relative to an abutment member during movement along the colon, and thus avoids any resulting frictional resistance to movement.

In addition, as shown by FIGS. 5 and 6, the folded portions 72 of the sheath are spaced axially from the inflatable region 66. As the abutment element is urged along the colon, together with the colonoscope 74 which is drawn with it, the inflatable region 66 of the sheath is increased in length by material from the folded portions. This increase in length is progressive and takes place by the sequential removal of the folded portions 72 from the abutment element 80, commencing with the radially innermost portion. These folded portions move into and become part of the inflatable portion 66 of the sheath by passing through a radially extending interconnecting sheath portion 100 located intermediate the inflatable region 66 and the folded portions. This interconnecting portion lies immediately behind the abutment element 80.

As may be seen from the above, the sheath inflates in an axial direction along the colon without eversion occurring together with any attendant frictional resistance to movement which eversion may cause. To withdraw the device, deflation of the sheath is required. The sheath 66, the abutment element 80 and the rigid structure may be relatively inexpensive as they have simplicity of construction, as in the first embodiment. As a result, they may readily be discarded after use.

In a modification of the third embodiment (not shown) the annular extension region of the sheath does not have sequentially interconnected and axially extending overlying folded portions. Instead, in the modification the annular extension region is crumpled similar to the crumpled annular extension region of the second embodiment. This provides sequentially interconnected sheath parts of random size, shape and direction, these sheath parts being held within cylindrical part 78 of the abutment element. During movement of the colonoscope device along a colon, the sheath parts move sequentially through the interconnecting sheath portion 100 to become parts of the lengthening inflated inflatable region of the sheath.

What is claimed is:

1. A device for movement along a passage, comprising:
an elongate tool having a major axis, distal and proximal end regions, and a sheath abutment element at the distal end region of the tool;
an elongate annular inflatable sheath surrounding the tool, the sheath having an annular inflatable region disposed between the abutment element and the proximal end region of the tool, and an annular extension region for the annular inflatable region, the annular extension region having a plurality of sequentially interconnected sheath parts extending from the inflatable region, the sheath parts being relatively oriented to face each other to locate the annular extension region around the distal end region of the tool with the annular extension region movable forwardly together with the distal end region of the tool;
an annular inflation chamber defined between the inflatable region and the outer surface of the tool; and
means to introduce pressurized fluid into the chamber to inflate the inflatable region of the sheath, when inside the passage, and to cause inflationary pressure then to act against the sheath abutment element to move the tool forwardly along the passage accompanied by sequential reorientation of the sheath parts and their sequential movement into and lengthen the inflated inflatable region.

2. A device according to claim 1, intended for medical use, and wherein the passage is a passage of a living being and, upon inflation, the sheath has limited radial expansion consistent with minimizing stress to the subject when inflated within the passage.

3. A device according to claim 2, wherein the annular extension region is connected to the annular inflatable region of the sheath by a distal end fold of the sheath, the extension region movable by eversion through the distal end fold into the inflated inflatable region.

4. A device according to claim 3, wherein the distal end fold of the sheath is engageable with the sheath abutment element so as to roll forwardly under inflation forces against the abutment element during movement of the sheath parts into the inflated inflatable region, to urge the tool forwardly.

5. A device according to claim 3 wherein the annular extension region is supported upon the distal end region of the tool.

6. A device according to claim 5 wherein the annular extension region is contained within a cylindrical housing secured to and around the tool, the housing having a distal end at which the housing provides an opening for release of the sheath parts as they move into the annular inflatable region.

7. A device according to claim 2 wherein the sheath parts of the annular extension region comprise a plurality of sequentially interconnected annular folded portions positioned around the distal end region of the tool, the folded portions being caused to sequentially unfold as inflationary pressure acts against the sheath abutment element so as to move the folded portions into and lengthen the inflated inflatable region.

8. A device according to claim 7, wherein each folded portion extends axially and the folded portions are relatively positioned radially outside of, and superposed upon, one another.

9. A device according to claim 8, wherein the annular extension region is connected to the annular inflatable region of the sheath by a distal end fold of the sheath, the folded portions, during unfolding, being moveable sequentially by eversion through the distal end fold to move them into and lengthen the inflated inflatable region.

10. A device according to claim 9, wherein the annular extension region is connected to the inflatable region of the sheath to effect unfolding of the folded portions radially inwards from the radially outermost folded portion.

11. A device according to claim 2 wherein the annular extension region is crumpled to form the sheath parts, crumpling of the annular extension region progressively caused to be removed as inflationary pressure acts against the sheath abutment element so as to move the sheath parts into and lengthen the inflated inflatable region.

12. A device according to claim 2, wherein the sheath has a minimum radius of collapse which is greater than any radial dimension of a region of the tool which is located radially within the annular extension region, and means is provided radially outwards of the annular extension region to hold the annular extension region and maintain the sheath parts spaced from that region of the tool by an annular gap.

13. A device according to claim 12, wherein the annular gap provides a part of the annular inflation chamber with the sheath abutment element having a surface defining a distal end of the gap whereby, during inflation, pressurized fluid within the inflation chamber acts through the gap against the sheath abutment element to draw the tool forwardly.

14. A device according to claim 13, wherein the means to hold the annular extension region comprises an axially extending part of the abutment element, the axially extending part containing and supporting the sheath parts to restrain them from radially outwards expansion, as a group, under inflation pressure and until each sheath part has moved into the inflated inflatable region, and the annular extension region is located forwardly of the inflatable region of the sheath, a radially extending sheath portion being located intermediate and interconnecting the inflatable region and the annular extension region.

15. A device for movement along a passage, comprising:

an elongate tool having a major axis, distal and proximal end regions, and an annular inflatable sheath abutment element at the distal end region of the tool;

an elongate annular inflatable sheath surrounding the tool, the sheath having an annular inflatable region disposed between the abutment element and the proximal end region of the tool and an annular extension region interconnected with the annular inflatable region;

an annular inflation chamber defined within the annular inflatable region of the sheath; and means to introduce pressurized fluid, both into the chamber to inflate the inflatable region of the sheath and into the sheath abutment element, when inside the passage, and with the abutment element inflated, to cause inflationary pressure to act against the sheath abutment element to draw the tool forwards along the passage accompanied by progressive movement of the annular extension region of the sheath into and lengthen the inflated inflatable region.

16. A device according to claim 15, intended for medical use, and wherein the passage is a passage of a living being, and upon inflation, the sheath and the sheath abutment element both have limited radial expansion consistent with minimizing stress to the subject when inflated within the passage.

17. A device according to claim 16, wherein the sheath and the sheath abutment element are inflatable to approximately equal outside diameters.

18. A device according to claim 17, wherein the sheath abutment element comprises a flexible annular wall surrounding the distal end region of the tool, the annular wall having upstream and downstream ends which are sealingly attached to the tool.

19. A device according to claim 17, wherein the sheath abutment element has a coating of a friction reducing material.

20. A device according to claim 17, wherein the annular inflatable region of the sheath and the sheath abutment element are simultaneously inflatable and, after inflation of the sheath abutment element, the sheath is operable under continued sheath inflation, to act against the sheath abutment element to force the sheath abutment element along the passage to draw the tool along the passage.

* * * * *

UNITED STATES PATENT AND TRADEMARK OFFICE
CERTIFICATE OF CORRECTION

PATENT NO. : 6,702,735 B2
DATED : March 9, 2004
INVENTOR(S) : Leonard Kelly

It is certified that error appears in the above-identified patent and that said Letters Patent is hereby corrected as shown below:

Title page,
Item [60], Related U.S. Application Data, should read -- [60] Provisional application No. 60/240,846, filed Oct. 17, 2000 --

Signed and Sealed this

Twenty-fourth Day of August, 2004

JON W. DUDAS
*Director of the United States Patent and Trademark Office*